(12) United States Patent
Petersen

(10) Patent No.: US 9,114,077 B2
(45) Date of Patent: Aug. 25, 2015

(54) NANOCRYSTALS FOR USE IN TOPICAL COSMETIC FORMULATIONS AND METHOD OF PRODUCTION THEREOF

(75) Inventor: Rolf Petersen, Berlin (DE)

(73) Assignee: ABBVIE DEUTSCHLAND GMBH & CO KG, Weisbaden (DE)

(*) Notice: Subject to any disclaimer, the term of this patent is extended or adjusted under 35 U.S.C. 154(b) by 788 days.

(21) Appl. No.: 12/514,621

(22) PCT Filed: Nov. 19, 2007

(86) PCT No.: PCT/EP2007/009943
§ 371 (c)(1),
(2), (4) Date: May 13, 2009

(87) PCT Pub. No.: WO2008/058755
PCT Pub. Date: May 22, 2008

(65) Prior Publication Data
US 2010/0047297 A1 Feb. 25, 2010

Related U.S. Application Data

(60) Provisional application No. 60/866,233, filed on Nov. 17, 2006.

(51) Int. Cl.
*A61Q 19/00* (2006.01)
*A61K 8/34* (2006.01)
(Continued)

(52) U.S. Cl.
CPC . *A61K 8/06* (2013.01); *A61K 8/044* (2013.01); *A61K 8/347* (2013.01); *A61K 8/602* (2013.01); *A61K 8/676* (2013.01); *A61Q 19/00* (2013.01); *B82Y 5/00* (2013.01); *A61K 2800/413* (2013.01); *A61K 2800/524* (2013.01)

(58) Field of Classification Search
None
See application file for complete search history.

(56) References Cited

U.S. PATENT DOCUMENTS 4,801,455 A * 1/1989 List et al. .............. 424/400
5,145,684 A 9/1992 Liversidge
(Continued)

FOREIGN PATENT DOCUMENTS

EP 0535972 A 4/1993
EP 0605497 1/1996
(Continued)

OTHER PUBLICATIONS

Miksicek, RJ, "Commonly occurring plant flavonoids have estrogenic activity," Molecular Pharmacology, Jul. 1993 vol. 44 No. 1, pp. 37-43.*

(Continued)

*Primary Examiner* — Rachel E Bredefeld
*Assistant Examiner* — Lisbeth C Robinson
(74) *Attorney, Agent, or Firm* — Jeffrey S. Melcher; Manelli Selter PLLC

(57) ABSTRACT

Provided are cosmetic preparations for topical application containing nanocrystals of cosmetic actives leading to an increased bioactivity of the molecules in the skin and methods of making the cosmetic preparations. The nanocrystals can be added to any cosmetic topical formulation, e. g. creams, lotions and liposomal dispersions. The drug nanocrystals are produced by a combination process of low energy pearl milling followed by a high energy high-pressure homogenization leading to nanocrystal suspensions (nanosuspensions) of improved physical stability.

26 Claims, 1 Drawing Sheet

(51) Int. Cl.
*A61K 8/04* (2006.01)
*A61K 8/60* (2006.01)
*A61K 8/67* (2006.01)
*A61K 8/06* (2006.01)
*B82Y 5/00* (2011.01)

(56) References Cited

U.S. PATENT DOCUMENTS

| | | | |
|---|---|---|---|
| 5,827,539 A * | 10/1998 | Gellenbeck | 424/489 |
| 5,858,410 A | 1/1999 | Muller | |
| 5,925,684 A * | 7/1999 | Schweikert et al. | 514/458 |
| 6,767,396 B2 * | 7/2004 | McElligott et al. | 106/453 |
| 6,814,959 B1 * | 11/2004 | Muller et al. | 424/59 |
| 6,979,440 B2 | 12/2005 | Shefer | |
| 7,067,152 B2 | 6/2006 | Shefer | |
| 2002/0142017 A1 | 10/2002 | Simmonnet | |
| 2005/0023386 A1 * | 2/2005 | Haskell | 241/16 |
| 2008/0311209 A1 * | 12/2008 | Beumer et al. | 424/489 |

FOREIGN PATENT DOCUMENTS

| | | |
|---|---|---|
| GB | 2200048 | 1/1988 |
| GB | 2269536 | 1/1994 |
| WO | 96/14830 | 5/1996 |
| WO | 00/67728 | 11/2000 |
| WO | 00/67800 | 11/2000 |
| WO | 01/03670 | 1/2001 |
| WO | 03/035031 A | 5/2003 |
| WO | 03/045353 A | 6/2003 |
| WO | 2004/054549 A | 7/2004 |
| WO | 2007/000193 A | 1/2007 |

OTHER PUBLICATIONS

Moschwitzer, J., Achleitner, G., Pomper, H., Muller, R.H., "Development of an intravenously injectable chemically stable aqueous omeprazole formulation using nanosuspension technology," European Journal of Pharmaceutics and Biopharmaceutics, vol. 58, Issue 3, Nov. 2004, pp. 615-619.*
Kipp, International Journal of Pharmaceutics, 284: 109-122 (2004).*
Keck et al., European Journal of Pharmaceutics and Biopharmaceutics, 62: 3-16 (2006) (available on-line Aug. 2005).*
Lenhardt et al., The AAPS Journal, 10: 435-438 (2008).*
A. Akkar, et. al. "Nanosuspenions—ultra-fine dispersions of actives and pigments for cosmetics" Journal of Cosmetic Dermatology,Blackwell ●Science LID, [Online] vol. 1, 2003, pp. 149,154-155, XP002474830 Retrieved from the Internet: URL: http : //www. blackwel 1-synergy. com/dol /p df/1O.1046/j.1473-2165.2002.tO1-1--00061.x> [retrieved on Apr. 2, 2008].
Moschwitzer el al: "Spray coated pellets as carrier system for mucoadhesive drug nanocrystals" European Journal of Pharmaceutics and Biopharmaceuiics, Meopharm Scientific Publ,, Stuttgart, DE, vol. 62, No. 3, Apr. 2006, pp. 282-287, XP005324595 ISSN: 0939-6411 cited in the application 2.2. High pressure homogenization/preaparation of the layering dispersion.
Wissing S A el al: "Solid Lipid Nanoparticles (SLN)—A Novel Carrier for UV Blockers" Pharmazie, Die, Govi Verlag, Eschborn, Dt, vol. 56, No. 10, 2001, pp. 783-786, XP001147308 ISSN: 0031-7144 the whole document.
Mueller R H el al ~"Nanosuspenslons as particulate drug formulations in therapy: Rationale for development and what we can expect for the fUture" Advanced Drug Delivery Reviews, Amsterdam, NL, vol. 47 No. 1, 2001, pp. 3-19, XP002232883 ISSN: 0169-409X Large, p. 15, col. 1-p. 17, col. I.
Mizutani et.al, Biochem Biophys Res Commun. Jul. 21, 2000; 274(1) :61-7). Discussed on p. 2 of application.
Müller, R. H., Akkar, A., Drug nanocrystals of poorly soluble drugs, in: Encyclopedia of Nanoscience and Nanotechnology H. S. Nalwa, ed.), American Scientific Publishers, 627-638, 2004. Discussed on p. 3 of application.
Muller, R. H., Böhm, B. H. L., Grau, M. J., Nanosuspensions—a formulation approach for poorly soluble and poorly bioavailable drugs, in: Handbook of Pharmaceutical Controlled Release Technology (Wise, D., ed.), 345-357, 2000. Discussed on p. 3 of application.
G. G. Liversidge and K. C. Cundy, "Particle Size Reduction for Improvement of Oral Bioavailability of Hydrophobic Drugs: I. Absolute Oral Bioavailability of Nanocrystalline Danazol in Beagle Dogs," Int. J. Pharm. 125 (1), 91-97 (1995). Discussed on p. 4 of application.
J. Heykants, et al., "The Pharmacokinetics of Itraconazole in animals and man", Recent Trends in the Discovery, Development and Evolution of AnitfungalAgents, R. A. Fromtling(Ed) 1987. Discussed on p. 4 of application.
D. Andes, et al., "In vivo pharmacodynamicsof antifungal drugs in treatment of candidiasis", Antimicrob Agents and Chemotherapy, Apr. 2003, 1179-1186. Discussed on p. 4 of application.
Rabinow et el., Enhanced Efficacy of Nanoedge Itraconazole Nanosuspension in an immunosuppressed rat model infected with an Itraconazole-resistant *C. Albicans* Strain, Abstract of AAPS Annual meeting in Salt Lake City, Utah, 2003. Discussed on p. 4 of application.
Hubinger et al, Determination of Retinol, Retinyl Palmitate and Retinoic Acid in Consumer Cosmetic Products, 12th FDA Annual Science Forum, Apr. 18-20, 2006. Discussed on p. 12 of application.
Grau, M. J., Kayser, 0., Müller, R. H., Int. J. Pharm.196, 155-157, 2000. Discussed on p. 13 of application.
Jacobs, C, Kayser, O., Muller, R. H., Int. J. Pharm. 214, 3-7, 2001. Discussed on p. 13 of application.
Jacobs, C, Müller, R. H., Pharmaceutical Research 19 (2), 189-194, 2002. Discussed on p. 13 of application.
Wissing, S. A., Lippacher, A., Müller, R. H., International Journal of Cosmetic Sciences 52, 313-324, 2001. Discussed on p. 19 of application.
Móschwitzer, J. , Müller, R. H., Spray coated pellets as carrier system for mucoadhesive drug nanocrystals, Eur. J. Pharm. Biopharm. 62, 282-287, 2006. Discussed on p. 26 of application.

* cited by examiner

NANOCRYSTALS FOR USE IN TOPICAL COSMETIC FORMULATIONS AND METHOD OF PRODUCTION THEREOF

CROSS-REFERENCE TO RELATED APPLICATIONS

This application claims priority to U.S. Provisional Application No. 60/866,233, filed Nov. 17, 2006, the complete disclosure of which is incorporated herein by reference. This application is the U.S. National Phase of International Application No. PCT/EP2007/009943, filed 19 Nov. 2007 designating the United States.

FIELD OF INVENTION

Provided are cosmetic preparations for topical application containing nanocrystals of cosmetic actives leading to an increased bioactivity of the molecules in the skin and methods of making the cosmetic preparations.

BACKGROUND OF THE INVENTION

Many compounds with in vivo effects of high interest for cosmetic formulations, e. g. antioxidants, are poorly soluble, which inhibits or excludes their use for cosmetic products. Examples are Rutin and Hesperidin, having antioxidant properties. The "natural" molecules possess highest activity, but they do not reach in vivo a sufficient effect because of their poor solubility. Therefore, one is forced to use derivatives which are biologically distinctly less efficient but are water-soluble or oil-soluble, and can therefore be dissolved in the water or oil phase of cosmetic preparations, e. g. cosmetic creams and lotions.

Another example is Resveratrol (3,4',5-trihydroxystilbene), a polyphenol found for example in the skins of red grapes. Resveratrol has anti-infective, antioxidant and anti-inflammatory properties. In addition, it is collagen-protective. It supports existing collagen structures and inhibits collagen-degrading enzymes (Mizutani et. al, Biochem Biophys Res Commun. Jul. 21, 2000; 274 (1):61-7).

One approach for the use of such compounds is their incorporation in polymeric or hydrophobic microparticles or nanoparticles. One commercial product is NanoSal™ Resveratrol, proprietary technology of the company Salvona Consumer Care (U.S. Pat. No. 7,067,152 and U.S. Pat. No. 6,979,440). The particles are offered as system enabling the release of the active over an extended period of time, which means a prolonged release system. However, such systems are contra productive because the prolonged release slows down the uptake by the skin due to concentrations of resveratrol in the water phase being below its saturation solubility. The molecules are captured in the particle matrix. Just the opposite would be desirable, to have a system releasing the active very fast leading to saturation or ideally supersaturation of the water phase. The supersaturation leads to an increased concentration gradient between the topical formulation and the skin and, thus, promoting the penetration of the active into the skin.

A pharmaceutical formulation approach to formulate poorly soluble drugs is nanocrystals. Drug nanocrystals are crystals with a size of a few nanometers up to 1000 nanometer. They can be prepared by bottom-up technologies and top-down technologies (Müller, R. H., Akkar, A., Drug nanocrystals of poorly soluble drugs, in: Encyclopedia of Nanoscience and Nanotechnology (H. S. Nalwa, ed.), American Scientific Publishers, 627-638, 2004, Müller, R. H., Böhm, B. H. L., Grau, M. J., Nanosuspensions—a formulation approach for poorly soluble and poorly bioavailable drugs, in: Handbook of Pharmaceutical Controlled Release Technology (Wise, D., ed.), 345-357, 2000). Bottom-up technologies are precipitation, the drug is dissolved in a solvent and this solution subsequently poured into a non-solvent leading to the so-called hydrosols (Sucker, et al., GB Patent 2200048, 1988; GB Patent 2269536, 1994) (product Nano-Morph™ by the company Soliqs, belonging to Abbott). In the top-down technologies, one starts from larger sized particle powders, diminution by several wet milling techniques leads to nanocrystals. In general the drug powder is dispersed in an aqueous or non-aqueous dispersion medium, containing a stabilizer (surfactant or polymeric stabilizer). This macrosuspension is subsequently milled for example by using a pearl mill (Liversidge, et al., U.S. Pat. No. 5,145,684, 1992) or passing the suspension through a high pressure homogenizer (Müller et al., PCT Application PCT/EP1995/004401, 1995, U.S. Pat. No. 5,858,410, 1999, PCT Application PCT/EP2000/006535, 2000). The nanosuspension is used as it is, for example for intravenous injection or, alternatively the dispersion medium is removed to obtain a dry nanocrystal powder, which is further processed for example to tablets.

The literature describes intensively the use of drug nanocrystals only for pharmaceutical formulations, i. e. for oral administration and for intravenous injection. After oral administration the bioavailability can be enhanced (Liversidge, et al., U.S. Pat. No. 5,145,684, 1992, G. G. Liversidge and K. C. Cundy, "Particle Size Reduction for Improvement of Oral Bioavailability of Hydrophobic Drugs: I. Absolute Oral Bioavailability of Nanocrystalline Danazol in Beagle Dogs," Int. J. Pharm. 125 (1), 91-97 (1995).), intravenous injection of drug nanosuspensions is able to reduce undesired toxic side effects of drugs. For example, the nephrotoxicity of the drug Itraconazole could be reduced distinctly by injection of Itraconazole nanosuspension ([1] J. Heykants, et al., "The Pharmacokinetics of Itraconazole in animals and man", Recent Trends in the Discovery, Development and Evolution of Anitfungal Agents, R. A. Fromtling (Ed) 1987. [2] D. Andes, et al., "In vivo pharmacodynamics of antifungal drugs in treatment of candidiasis", Antimicrob Agents and Chemotherapy, April 2003, 1179-1186, [3] Rabinow et el., Enhanced Efficacy of Nanoedge Itraconazole Nanosuspension in an immunosuppressed rat model infected with an Itraconazole-resistant *C. Albicans* Strain, Abstract of AAPS Annual meeting in Salt Lake City, Utah, 2003). A recent review of the drug nanocrystal technology is presented by Müller et al. (Keck, C. M., Müller, R. H., Eur. J. Pharm. Biopharm. 62, 3-16, 2006). However, there is no data published proving that drug nanocrystals are beneficial when used in topical pharmaceutical formulations applied to the skin. Especially there are no hints that the biological activity of drugs in the skin is increased. Furthermore, there are no reports for cosmetic actives about increase of biological activity when the actives are used in a nanocrystalline form.

SUMMARY OF THE INVENTION

From theoretical considerations it was hoped to find potentially some positive effect of nanocrystalline cosmetic actives on the skin, but surprising was the extent of the observed effect. A Rutin nanosuspension with 5% Rutin as non-dissolved nanocrystals was applied to the skin of human volunteers and compared to a 5% solution of a water-soluble Alpha-G-Rutin PS regarding photoprotection of the skin (based on the antioxidant property of Rutin) (Example 15). In the aqueous nanosuspension, the solubility of Rutin was in the range of its saturation solubility being 0.0123% (Example 14), the water-soluble derivative was dissolved at 5%, that means the concentration of dissolved molecules was about 500 times higher compared to the nanosuspension. Despite the 500 times lower concentration of dissolved Rutin in the water phase of the nanocrystal suspension, the nanosuspension was about 25% more effective in photoprotection (MED of Rutin nanocrystals 1.59 versus 1.27 for 5% Rutin derivative solution) (Example 15). From this—despite the 500 times lower concentration—the concentration of actives formulated as nanocrystals in the skin were much higher compared to using a water-soluble derivative or using the active in normal powder form. Therefore, cosmetic actives in form of nanocrystals were found to increase in a very pronounced way the biological activity, without being bound by any theory, believed to be due to improved penetration into the skin.

These objectives are met by a method for producing a formulation for topical application to the skin or mucosal surfaces, comprising the steps of: suspending a powder comprising a cosmetic or pharmaceutical active in an aqueous or non-aqueous dispersion medium, preferably being at least one of an aqueous phase or lipidic phase of a monophasic system, an aqueous phase or lipidic phase of an oil-in water emulsion, water-in-oil emulsion, microemulsion, liposomal dispersion or a macrosuspension, and containing at least one stabilizer to produce a suspension; passing the suspension through a pearl or ball mill at least one pass to produce a pre-milled suspension; and subjecting the pre-milled suspension to high pressure homogenization at least one cycle to produce particles of a cosmetic or pharmaceutical active in the nanometer range (nanocrystals), having a PCS size below 1000 nm, being dispersed in at least one of an aqueous phase or lipidic phase of a monophasic system, an aqueous phase or lipidic phase of an oil-in water emulsion, water-in-oil emulsion, microemulsion, liposomal dispersion or a macrosuspension, wherein a concentration of the dispersed active in the aqueous phase (in case the nanocrystals are dispersed in the aqueous phase) or in the lipidic phase (in case the nanocrystals are dispersed in the lipidic phase) is above the saturation concentration of bulk active material in the respective phase.

The objectives are also met by a formulation for topical application to the skin or mucosal surfaces comprising: particles of a cosmetic or pharmaceutical active in the nanometer range (nanocrystals), having a PCS size below 1000 nm, being dispersed in at least one of an aqueous phase or lipidic phase of a monophasic system, an aqueous phase or lipidic phase of an oil-in water emulsion, water-in-oil emulsion, microemulsion, liposomal dispersion or a macrosuspension, wherein a concentration of the dispersed active in the aqueous phase (in case the nanocrystals are dispersed in the aqueous phase) or in the lipidic phase (in case the nanocrystals are dispersed in the lipidic phase) is above the saturation concentration of bulk active material in the respective phase.

The invention provides cosmetic or pharmaceutical formulation which can be applied to the skin or mucosal surfaces (e. g. mucosa in the mouth, vaginal mucosal surfaces, mucosa of the eye) containing the cosmetic or pharmaceutical active as a particle with a size in the nanometer range (either amorphous or crystalline nanocrystals), such formulations being gels, o/w creams or w/o creams, aqueous suspensions (aqueous lotions) or non-aqueous suspensions (anhydrous lotions) or sprays.

DETAILED DESCRIPTION OF THE INVENTION

Figure 1:
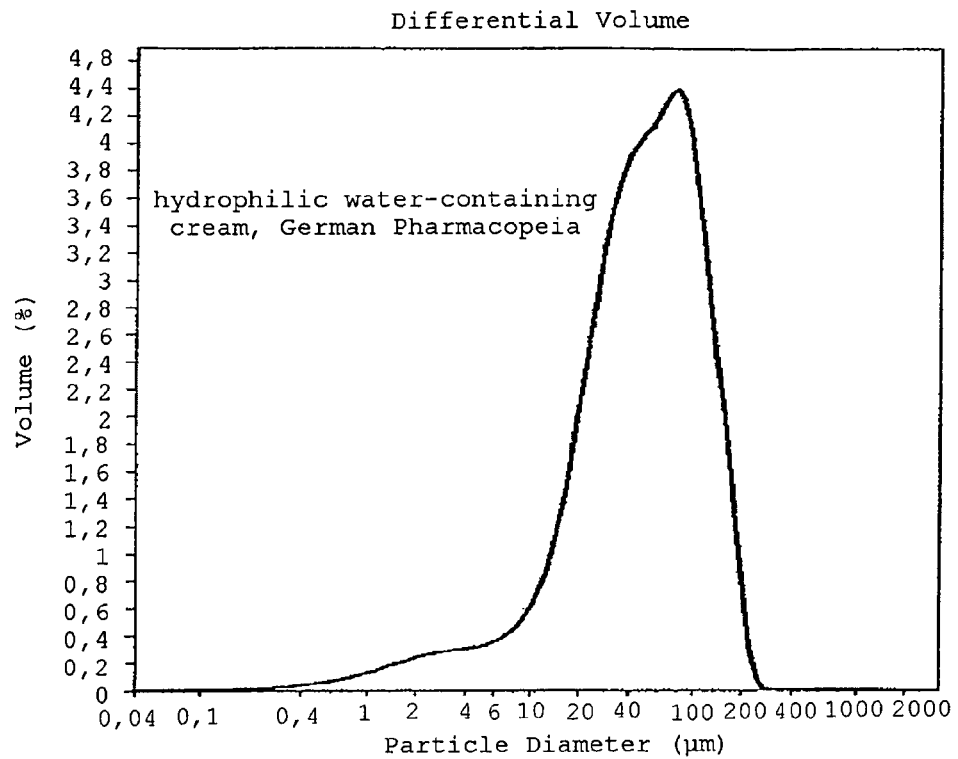
FIG. 1 illustrates the droplet size distribution of hydrophilic water-containing cream.

For the production of nanocrystals of cosmetic actives all the methods can be employed described in the literature for pharmaceutical drug nanocrystals; that means precipitation in various variations and size reduction methods such as pearl milling, high pressure homogenization and spray drying. For the production of the cosmetic nanocrystals, high pressure homogenization only (examples 1-4) or a combination of pearl milling and high pressure homogenization was employed (examples 8 and 9), either dispersing the drug powder in water containing a stabilizer or alternatively dispersing the product powder in water mixtures (e. g. water-glycerol).

Particle size analysis was performed using photon correlation spectroscopy (PCS, Malvern Zetasizer 4 or Zetasizer Nano-ZS, Malvern Instruments, United Kingdom). The PCS yields the diameter of the bulk population (z-average) and a polydispersity index (PI). The samples were diluted with bidestilled water to reach an appropriate concentration for the measurement, as indicated by the PCS instrument. Two measurement runs were conducted, each consisting of 10 single measurements, and then a mean was calculated. The PI is a measure for the width of the size distribution. In addition, especially to monitor the physical stability, laser diffractometry (LD) was used. Employed was a Beckman-Coulter LS 230 (Beckmann Coulter, USA). The measurements were performed using the Mie theory for the submicron range and the Fraunhofer theory to analyze particles in the micrometer size range, especially detection of aggregates of nanocrystals.

The nanosuspensions produced had mean PCS diameters in the range of approx. 300 nm to 800 nm. They possess a viscosity similar to water and can be applied to the skin either as they are or alternatively viscosity enhancers can be added such as xanthan gum, high molecular weight poloxamer molecules (e. g. Poloxamer 338, 407) or polyacrylates (e. g. Carbopol 981). Analysis of the nanocrystals in the gels by laser diffractometry revealed that the crystals remained finely dispersed, there was no or very limited aggregation. Gels are therefore one suitable topical formulation for application of nanocrystals to the skin.

Alternatively the nanosuspensions can be admixed to the water phase of o/w creams or o/w lotions. An adequately concentrated nanosuspension can be, for example, simply admixed to the cream or lotion by gentle blending with a stirrer. Admixing can be performed directly after production at elevated temperature or during the cooling process, e. g. at 30° C., or after the cooling process at room temperature (Example 17). Laser diffractometry analysis could show that the nanocrystals remained intact in the formulation; a second nanocrystal peak in the nanometer range was detected apart from the major peak of oil droplets in the micrometer range. Nanocrystals can also be added to the inner water phase of cosmetic formulations, e. g. w/o/w emulsions, microemulsions or the inner water phase of liposomes (waterphase in the liposome core).

Alternatively the nanocrystals can be dispersed in non-aqueous liquids, e. g. oils, such as medium chain triglyceride (MCT) oils or liquid paraffins. These preparations could be applied in very dry skin conditions or in case a water-repellent effect is desired. In such cases, the nanocrystals would not be produced in water. Preferentially they are diminuted directly in these non-aqueous liquid media.

The Rutin and the Hesperidin nanosuspensions were investigated in vivo regarding their photo-protective potential compared to solutions of a water-soluble Rutin conjugate with saccharide (example 15). Topical application of the antioxidants should increase the dose required to generate a UV erythem. The higher the photo-protective effect, the higher will be the increase in the MED for UV erythem generation. Based on the ratio MED of treated area/MED untreated area a sun protection factor can be calculated. As a reference standard, alpha-tocopherol acetate was used, being known as effective anti-oxidant. To very well differentiate in efficiency between the preparations, the formulations were applied only over 4 days (day 1, 2, 3 and 4) and only once a day. Under these conditions—short treatment time and only once a day application—the anti-oxidant reference standard was not effective because of its obvious too low bioactivity after short treatment duration. The calculated SPF was 0.85, indicating even an increase in sensitivity for UV erythems. The untreated area was less sensitive to UV radiation than the area treated with alpha-tocopherol acetate. The water-soluble Rutin saccharide showed a UV protective effect with an SPF of 1.27. It has to be noted that the selected concentration of Rutin saccharide was equivalent to 5% Rutin. (Percentage of Rutin in the Rutin saccharide molecule is about 80%, 20% are the saccharides.) The concentration of dissolved Rutin in the Rutin nanosuspension is equivalent to the water solubility of nanocrystalline Rutin that means its saturation solubility of 0.0123% (example 14). Despite the fact that the dissolved Rutin in the Rutin nanosuspension was about 500 times lower (5.0% for Rutin saccharide compared to 0.01% Rutin nanosuspension), the Rutin nanosuspension increased the SPF to 1.59. That means that only with 1/500 concentration of dissolved molecules, the Rutin nanosuspension was about 25% more effective than Rutin saccharide.

Addition and dissolution of 5% of a solid compound to dermal cosmetic formulations is usually not desirable because after application of the product to the skin and evaporation of the water from the formulation, solid compound will remain as fine powder on the skin. This can impair the aesthetic appearance and might be acceptable for pharmaceutical formulations with the aim of treating diseases, but usually not for a highly aesthetic cosmetic formulation. The nanocrystals allow using a much lower concentration of active compared to water-soluble active derivatives. In the case of Rutin it is not necessary to have 5% Rutin nanocrystals in the formulation as tested in example 7. It is sufficient to have just an amount of nanocrystals in a formulation to make sure that enough crystalline compound is available for dissolving to replace the active penetrated from the water phase into the skin. That means in case of a saturation solubility in the range of 0.01%, a nanocrystal concentration of 0.05% to 0.10% in the formulation is fully sufficient in most cases. That means the concentration of active can be reduced by e. g. a factor of 50-100. This leads to a much better aesthetic appearance because of the lower solid content of the formulation. In addition, the drug nanocrystals are so small that they are not being noticed on the skin in contrast to a powder film of crystallized soluble active after water evaporation. In addition, the lower concentration is of high interest in case of very expensive cosmetic actives (e. g. Apigenin with a price for 1 kg of around 1,000 US$ in 2006). Furthermore, it is well known that for many cosmetic actives the original molecules possess a higher activity compared to chemical derivatives, e. g. retinol versus retinyl palmitate (Hubinger et al, Determination of Retinol, Retinyl Palmitate and Retinoic Acid in Consumer Cosmetic Products, $12^{th}$ FDA Annual Science Forum, Apr. 18-20 2006), in case they can be made bioavailable to the skin as it has been achieved in the present invention.

Nanosuspensions are a highly dispersed system. The energy of the system increases with the interfacial surface area ($E=\gamma A$, E—Energy of the system, $\gamma$—interfacial tension, A—interfacial surface area). Therefore, such systems are unstable, the particles tend to significantly aggregate. Aggregation is especially pronounced in case electrolytes are present in the system leading to reduction of the zeta potential, subsequently to a reduction of electrostatic repulsion and therefore physical instability. Especially in many cosmetic formulations which contain electrolytes, for example, salts or as dissociating dissolved actives. Therefore, it is highly desirable to have nanocrystal suspensions available with improved physical stability.

Production of nanocrystals by high-pressure homogenization is a relatively tedious process; in general 10 to 20 homogenization cycles are required. In case larger quantities have to be produced, this leads to long homogenization times with wearing of the machine, because high-pressure homogenization is a high energy diminution process. The starting material for producing the nanocrystals was crude (e. g. up to 50-100 µm). Therefore, to avoid even higher numbers of homogenization cycles than 20, when starting from such a crude material, the active was dispersed in a stabilizer solution and pre-milled using a pearl mill, typically to mean sizes of about 1 to a few µm. Then high pressure homogenization was applied, that means a combination production technology was used by combining low energy pearl milling to reduce the particle size initially, followed by high energy high-pressure homogenization, typically 1 to 5 homogenization cycles (examples 8 and 9). Surprisingly it was found that after this pre-treatment only one homogenization cycle—in contrast to the published up to 20 cycles ([1.] Grau, M. J., Kayser, O., Müller, R. H., Int. J. Pharm. 196, 155-157, 2000, [2.] Jacobs, C., Kayser, O., Müller, R. H., Int. J. Pharm. 214, 3-7, 2001, [3.] Jacobs, C., Müller, R. H., Pharmaceutical Research 19 (2), 189-194, 2002)—was sufficient to achieve a nanocrystalline product, whereby the drop in size compared to the starting material was very pronounced by several hundred nanometers in one cycle (example 8). Even more surprising was the fact, that lower pressures (100-1000 bar) proved in most cases almost as effective as the high pressure (1500 bar) (Example 9) or even more effective (Example 8).

Surprisingly it was further discovered that these nanosuspensions were much more stable during long-term storage and more electrolyte-stable compared to the nanocrystals produced by pearl-milling only (Example 13). The Apigenin nanocrystals—only pre-milled and pre-milled and homogenized (Example 9)—were admixed to electrolyte concentrations known to cause zeta potential reduction and aggregation (calcium chloride, $CaCl_2$). The resulting increase in size directly after admixing was analyzed by laser diffractometry. Nanosuspensions produced by pearl milling only showed a much more pronounced increase in size than the nanocrystals from the combination process pearl milling plus subsequent homogenization. There was very limited or no size increase as determined by monitoring appropriate formation using laser diffractometry (Example 14).

The nanocrystals can be additionally stabilized in crystal size against crystal growth by adding the in the literature described crystal growth inhibitors such as PVA (polyvinyl alcohol), PVP (polyvinyl pyrrolidone), cellulose derivatives such as MC (methylcellulose), HPMC (hydroxypropylmethylcellulose) and HPMCAS (hydroxypropylmethylcellulose-acetatesuccinate) and/or nucleation inhibitors such as bile salts, to inhibit nucleation in the supersaturated dispersion medium of the nanosuspension.

Furthermore it was surprisingly found that it is not necessary to process the pearl milled nanosuspension with high-homogenization pressures such as 1500 bar, to obtain a nanosuspension with improved electrolyte stability. It was completely sufficient to process the nanosuspensions at low homogenization pressures in the area of 100-1000 bar. The subsequent homogenization at low pressures had a pronounced effect of reducing the particle size, but also further improved the physical stability of the nanosuspensions.

To summarize, a combination of pearl milling with subsequent high pressure homogenization leads to nanosuspensions with improved physical stability on long-term and against electrolytes, consequently improved stability in general. The pearl pre-milling can be performed to a size of a few micrometer (typically 1-5 μm, diameter 50% of laser diffractometry, volume distribution) or alternatively to the upper nanometer range (e. g. 400-1000 nm). The subsequent high pressure homogenization process can be performed at higher pressures (e. g. 1000 or 1500 bar, in special cases 2000 bar to 4000 bar) leading not only to improved physically stable nanosuspensions but simultaneously also to a further reduction in size for most cosmetic actives. Alternatively, the high pressure homogenization can be performed at lower pressures (e. g. 100 to 400 bar, in special cases 400-700 bar) effecting less the diameter of the bulk population (PCS data). Preferably, the high pressure homogenization is conducted at a pressure which avoids temperature peaks that cause substantial irreversible aggregation of the selected active.

At the beginning, homogenization of actives was performed applying no temperature control. Despite an increase in the temperature of close to 100° C. during the homogenization process, the particle size was not affected (e. g. for Rutin, example 5). However, for other compounds, it was surprisingly found that the temperature affected extremely the physical stability during homogenization. Apigenin tended to form aggregates (Example 6), which were irreversible by subsequent homogenization. For Apigenin, it proved to be preferable to keep the temperature during the complete homogenization process below 20° C., preferentially below 10° C. and ideally in the range between 5 and 0° C. The same effect was observed for Resveratrol. Therefore in a special version of the invention, for some compounds, the process should be performed at a temperature which avoids substantial irreversible aggregation of the active, for example, below room temperature, especially below 10° C. and preferentially below 5° C. or even at 0° C. (Example 4).

The nanocrystals are an ideal formulation for poorly soluble actives, primarily for actives having a solubility below 10 mg/ml, even better below 1 mg/ml, especially below 0.1 mg (100 μg)/ml, the relative solubility increase according to the Kelvin equation being most pronounced for very poorly soluble compounds, i.e. below 10 μg/ml or even below 1 μg/ml, measured at room temperature (25° C.).

The solubility is increasing with decreasing size of the crystals. From this, the mean PCS size of the crystals has to be below 1 μm (1,000 nm), preferentially lower than 500 nm or even more preferably below 200 nm, being optimal for highest solubility increase below 100 nm and showing highest solubility in the range of 20-50 nm.

Cosmetic actives of interest as drug nanocrystals include the groups of polyphenols, such as Catechines (like epicatechine, epicatechine-3-gallat, epigallocatechine, epigallocatechine-3-galla), flavonoids (like Luteolin, Apigenin, Rutin, Qercitin, Hesperidin, Fisetin, Rhametin), isoflavones (like Genistein, Daidzein, Glycitein, Prunetin), cumarines (like Daphnetin, Umbelliferon), further Emodin, Resveratrol, Oregonin.

Of cosmetic interest are triterpenes with anti-inflammatory activity like *Boswellia*, extracts from *Centella asiatica*, namely asiaticoside, aisatic acid, madecassic acid or 18β-glycyrrhetinic acid.

Of additional cosmetic interest are molecules like Andographolide, Forskolin, Glabridin, Mangiferin, gamma-Oryzanol, vitamin derivatives like ascorbyl palmitate, retinyl palmitate.

Of interest as well are cosmetic actives which possess a relatively high water-solubility but show insufficient penetration into the skin, for example caffeine. The caffeine penetration into the skin increases with increasing concentration of dissolved caffeine in the topical formulation. The rate limiting step is not the skin but the available caffeine concentration in the topical formulation. Therefore, in topical caffeine formulations one can add caffeine nanocrystals as an additional depot to replace caffeine in the water phase, which is penetrated into the skin.

The production method is not restricted only to cosmetic poorly soluble compounds for generating nanocrystals but also for other actives, e.g. pharmaceuticals (drugs), nutraceuticals and food supplements (e. g. coenzyme Q10). Thus, the method is not restricted to cosmetic poorly soluble compounds, but also useful for pharmaceutical products. This can be seen for the compound rutin. Rutin is a cosmetic active, at the same time rutin is used as a drug in pharmaceutical products. Therefore the increase in the rutin concentration in the skin is also beneficial for pharmaceutical applications. The same is valid for other poorly soluble drugs, e. g. antimycotics, such as itraconazole. For efficient treatment of skin infections, a carrier formulation containing rutin in liposomes proved to be much more effective than having rutin in a normal cream (Econazol Lipogel versus cream, treatment was three times faster). In contrast to the liposomal rutin, in nanocrystal formulations the saturation solubility of rutin is increased, thus leading to increased penetration and higher concentrations in the skin accelerating treatment.

In a special version of cosmetic formulations, the nanocrystals can be incorporated in cosmetic dermal formulations, such as creams and lotions which contain additionally solid lipid nanoparticles (SLN) (Müller and Lucks, European Patent No. 0605497, 1996) or nanostructured lipid carriers (NLC) (Müller et al., PCT Application PCT/EP2000/004111, 2000, PCT Application PCT/EP2000/004112, 2000). The lipid nanoparticles both SLN and NLC are known to form occlusive films on the skin further enhancing the penetration of actives into the skin (Wissing, S. A., Lippacher, A., Müller, R. H., International Journal of Cosmetic Sciences 52, 313-324, 2001). The penetration enhancing effect of the lipid nanoparticles can be combined with the special increase of bioactivity of cosmetic molecules achieved by nanocrystals.

The concentration of the nanocrystals used in the topical formulations depends on the saturation solubility of the active and the velocity of penetration into the skin. In general, the nanocrystal concentration should be minimum 3 to 5 times higher than the saturation solubility to ensure a sufficient depot for further dissolution of active. Preferentially, a 10 to maximum 50 times higher concentration is recommended in case the molecules penetrate fast into the skin once dissolved. In case of an active with a saturation solubility of 0.01% the nanocrystal concentration should be selected in the range approx. 0.05 to 0.10% for most actives. Based on the different solubilities, in most cases maximum nanocrystal concentrations are up to 10%, in general less than 5% and for most of poorly soluble actives in the range 0.1 to 1%. Identical to pharmaceutical pastes (e. g. zinc oxide), nanocrystal pastes with a high solid content can be produced. In such cases the solid content can range from approx. 20% to 50%, selection criterion for the percentage is a maintained spreadability of the paste onto the skin. Such higher concentrated nanocrystal pastes are also of interest for decorative cosmetics. In cosmetics, a higher solid content is desirable for actives which are coloured and can be used at the same time as 'coloured pigments' in decorative cosmetics (e. g. eye shadow, rouge, make-up, concealer). For pharmaceutical dermal products it can be of interest to have a higher concentration as longer-lasting drug depot, in case of fast penetrating molecules.

EXAMPLES

Example 1

Rutin nanosuspensions were produced by dispersing the Rutin powder in an aqueous solution of 1% surfactant. The dispersion was performed by using a rotor-stator stirrer T25 (ultra-turrax, Jahnke and Kunkel, Staufen, Germany), stirring for one minute at 8000 RPM. The obtained pre-suspension was then passed through a high pressure homogenizer Micron LAB 40 (APV Homogenizers, Unna/Germany). Applied were two homogenization cycles at 150 bar, 500 bar followed by 20 homogenization cycles at 1500 bar. The mean PCS diameter of the product was 783 nm, the polydispersity index 0.285. Laser diffractometry analysis (based on Mie theory) yielded a diameter 50% of 0.882 µm, a diameter 90% of 1.962 µm and a diameter 99% of 2.464 µm. Production was performed without temperature control. During production the temperature increased to about 60° C. When this temperature was reached, a cooling was performed to reach again room temperature. The increase of the temperature of the product did not lead to any aggregation as seen by the continuous decrease of the PCS diameter from one cycle to the next.

Example 2

Hesperidin nanosuspensions were produced as described in example 1. The diameter of the bulk population determined by PCS was 599 nm, the polydispersity index 0.312. The LD results were diameter 50% 0.383 µm, diameter 90% 1.568 µm and diameter 99% 2.404 µm. No temperature control was applied during homogenization, aggregation problems did not occur during production despite heating up of the suspension.

Example 3

Ascorbylpalmitate powder (6%) was dispersed in a solution of 0.3% Tween 80 using an ultra-turrax T25 (Jahnke and Kunkel, Staufen, Germany) at 8000 RPM for one minute. The obtained pre-suspension was homogenized using a Micron LAB 40 applying two homogenization cycles at 150, 500 and 1000 bar, respectively. After this pre-milling, 20 homogenization cycles were performed at 1500 bar. After 20 cycles at 1,500 bar, 0.7% Tween 80 were added to enhance the long-term stability of the nanosuspension, that means the total amount of Tween 80 in the formulation was 1.0%. The mean PCS diameter of the bulk population was 298 nm, the polydispersity index 0.234.

Example 4

Resveratrol nanosuspensions were produced by a high pressure homogenizer Micron LAB 40 (APV Homogenizers, Unna/Germany). Applied were two homogenization cycles at 150 bar, 500 bar followed by 20 homogenization cycles at 1500 bar. In the last process was followed by 2 homogenization cycles at 1500 bar to avoid particles aggregations. The mean PCS diameter of the product was 737 nm, the polydispersity index 0.463. Laser diffractometry analysis yielded a diameter 50% of 0.822 µm, a diameter 90% of 2.405 µm and a diameter 99% of 3.330 µm. Production was performed with temperature control at 0° C. If temperature increases above 10° C., it should be cooled until 0° C. to avoid aggregation.

Example 5

The Rutin nanosuspension from example 1 was homogenized as described in example 1 and the increase in temperature was monitored. Within cycle 1 to cycle 20 the temperature increased to 90° C. The diameters D 50% of laser diffractometry decreased continuously and were 1.210 µm, 1.101 µm, 0.968 µm and 0.882 for 5, 10, 15 and 20 respective cycles. That means there was no aggregation due to the increase in temperature.

Example 6

Apigenin nanosuspension was produced as described in example 1 for Rutin. The composition of the suspension to be homogenized was 5% apigenin, 2% surfactant and 93% water. During the production the temperature increased from room temperature to 40° C. from cycle 1 to cycle 5. The diameters 50% were 1.117 µm after cycle 1 and 1.570 µm after cycle 5. After further increase of the temperature the diameter 50% increased to 1.809 µm (cycle 10) and 2.188 µm (cycle 15). That means the suspension was highly susceptible to increased temperatures leading to pronounced aggregation. The same suspension was homogenized keeping the temperature below 10° C. This avoided the aggregation phenomenon. With increasing cycle numbers the diameter 50% decreased continuously from 0.637 µm (cycle 1) to 0.536 µm (cycle 5) and 0.398 µm (cycle 15). This shows that homogenization at lower temperatures avoids aggregation of certain substances.

Example 7

A suspension of the active Rutin was prepared by dispersing the Rutin powder by stirring in an aqueous phase containing Tween 80 and glycerol. The composition of the obtained suspension was Rutin 20.0%, glycerol 5.0% and Tween 80 2.0% (polyethylene sorbitanmonooleate) (all % ages are weight/weight). The suspension was passed 8 times through wet mill of the pearl mill type MS 18 (company FrymaKoruma, Neuenburg, Germany). The milling material was 0.65-0.80 mm (passes 1-4) and 0.3 mm (passes 5-8) pearls of zirconium oxide, the flow rate was approx. 20 kg per hour. The temperature of the suspension during wet milling was kept below 20° C. (Celcius) by cooling the suspension inbetween the passes.

The particle size was analyzed using photon correlation spectroscopy (PCS, Malvern Nanosizer) being 1005 nm.

Example 8

The pre-milled suspension from example 7 was diluted to a Rutin concentration of 5.0% by addition of water containing glycerol 5.0% and Tween 80 2.0%. That means the resulting suspension was composed of Rutin 5.0%, glycerol 5.0% and Tween 80 2.0%. This suspension was then passed once (1 cycle) through an Avestin C 50 homogenizer at 20° C. (Avestin Inc., Ottawa, Canada). Three suspensions were prepared by applying increasingly pressures of 100 bar, 1,000 bar and 1,500 bar, respectively. The PCS particle size was analyzed by PCS. Surprisingly the smallest size was obtained by applying the lowest pressure.

| Homogenisation pressure (bar) | PCS size Rutin | size decrease |
|---|---|---|
| non-homogenized (= pre-milled) | 1005 nm | — |
| 100 bar | 604 nm | −401 nm |
| 1,000 bar | 750 nm | −255 nm |
| 1,500 bar | 820 nm | −185 nm |

Example 9

A suspension of the active Apigenin was prepared by dispersing the Apigenin powder by stirring in an aqueous phase containing Tween 80 and glycerol. The composition of the obtained suspension was Apigenin 20.0%, glycerol 5.0% and Tween 80 2.0% (polyethylenesorbitanmonooleate) (all %ages are weight/weight). The suspension was passed 4 times through wet mill of the pearl mill type MS 12 (company FrymaKoruma, Neuenburg, Germany). The milling material was 0.3 mm pearls of zirconium oxide, the flow rate was 10 kg per hour. The temperature of the suspension during wet milling was kept below 5° C. (Celcius).

PCS analysis revealed a size of 670 nm of this pre-milled suspension. The pre-milled suspension was diluted to an Apigenin concentration of 5.0% by addition of water containing glycerol 5.0% and Tween 80 2.0%. That means the resulting suspension was composed of Apigenin 5.0%, glycerol 5.0% and Tween 80 2.0%. This suspension was then passed once (1 cycle) through an Avestin C 50 homogenizer at 20° C. (Avestin Inc., Ottawa, Canada). Three suspensions were prepared applying increasing pressures of 100 bar, 1,000 bar and 1,500 bar, respectively, size analysis of the three homogenized suspensions was performed by PCS. As in example 8, a pronounced decrease in size by 230 nm was obtained at a pressure as low as 100 bar. A ten times higher pressure of 1000 bar lead only to a further reduction by 115 nm to a PCS diameter at 325 nm. Again—as in example 8—applying the highest pressure was least efficient compared to the lower pressures of 1000 bar and 100 bar. Again a size increase from 325 (1000 bar) to 334 nm (1500 bar) was found.

| Homogenisation pressure (bar) | PCS size Apigenin | size decrease |
|---|---|---|
| non-homogenized (= pre-milled) | 670 nm | — |
| 100 bar | 440 nm | −230 nm |
| 1,000 bar | 325 nm | −345 nm |
| 1,500 bar | 334 nm | −336 nm |

Example 10

An Apigenin suspension was prepared in the concentration used for pearl milling as described in example 9. This suspension was then pre-milled—instead of pearl milling—using high pressure homogenization as described in the literature (Moschwitzer, J., Müller, R. H., Spray coated pellets as carrier system for mucoadhesive drug nanocrystals, Eur. J. Pharm. Biopharm. 62, 282-287, 2006). Two homogenization cycles were applied at 150 bar followed by 2 homogenization cycles at 500 bar, at 20° C.

PCS analysis revealed a mean PCS diameter of 800 nm. Then this pre-milled suspension was homogenized applying 100 bar, applying 20 homogenization cycles. Samples were drawn after 1, 3, 11, 15 and 20 cycles, measured by PCS and the decrease in PCS size calculated per cycle. In case more sampling was performed after multiple cycles, the measured decrease was divided by the number of cycles to obtain the average decrease per cycle, e. g. size decrease from cycle 11 to 15 by 82 nm achieved with 4 additional cycles. Size decrease per cycle is 82 nm divided by 4=20.5 nm. A pre-milled, other than using the pearl mill, did not lead to an efficient size decrease after applying one cycle at 100 bar. With pre-milling by homogenization only a drop in size to 864 nm was achieved, in case of pearl pre-milling a drop to 670 nm was achieved. Even applying more cycles at 100 bar to the product pre-milled by homogenization lead to very little further decrease (851 nm, cycle 11; 754 nm, cycle 20), the crystals still being distinctly larger than applying the combination method of pearl pre-milling and high pressure homogenization.

| cycle number (pressure 100 bar) | PCS size Apigenin | size decrease/increase per cycle (−/+) |
|---|---|---|
| pre-milled by homogenization | 1795 nm | — |
| Cycle 1 | 864 nm | −831.0 nm |
| 3 | 872 nm | +4.0 nm |
| 11 | 851 nm | −2.6 nm |
| 15 | 769 nm | −20.5 nm |
| 20 | 754 nm | −3.0 nm |

Example 11

The same was performed as described in example 10, but the homogenization pressure during the homogenization of the pre-milled Apigenin product was 1,500 bar. The combination of pearl pre-milling and applying just 1 cycle at 100 bar lead to a PCS size of 440 nm (example 9), that means the method of the invention is more efficient than (1) conventional combination of high pressure pre-milling and homogenization at high pressure, and
(2) more efficient at lower pressures than conventional high pressure homogenization of even high pressures (1500 bar),
(3) because only a size reduction to 699 nm was achieved with 1 cycle at 1500 bar. 15 cycles needed to be applied at 1500 bar to reach the same low diameter (439 nm).

| cycle number (pressure 100 bar) | PCS size Apigenin | size decrease/increase per cycle (−/+) |
|---|---|---|
| pre-milled by homogenization | 1795 nm | — |
| Cycle 1 | 699 nm | −1096.0 nm |
| 3 | 631 nm | −34.0 nm |
| 11 | 657 nm | +3.2 nm |
| 15 | 439 nm | −57.0 nm |
| 20 | 381 nm | −12.0 nm |

Example 12

Apigenin nanosuspension with the composition of 20.0% Apigenin, 2.0% Tween 80 and 78.0% water was pre-milled using a pearl mill from FrymaKoruma. The mean PCS diameter of the pre-milled product was 412 nm, PI 0.272. Five different nanosuspensions were produced by passing this pre-milled suspension one cycle at increasing pressure of 100, 300, 500, 1,000 and 1,500 bar. The size was analyzed by PCS:

| Homogenization pressure | mean PCS size | mean polydispersity index |
|---|---|---|
| pre-milled suspension (reference) | 412 nm | 0.272 |
| 100 bar | 286 nm | 0.293 |
| 300 bar | 275 nm | 0.264 |
| 500 bar | 275 nm | 0.316 |
| 1,000 bar | 284 nm | 0.272 |
| 1,500 bar | 279 nm | 0.246 |

Most efficient in reducing the size were the pressures 100 to 500 bar. Higher pressures at 1000 bar and 1500 bar yielded even slightly higher sizes than 500 bar. Considering that the pressure during homogenization leads to temperature peaks possibly affecting the chemical stability of the active, and that no relevant further decrease in size was achieved at higher pressures, the lowest pressure of 100 bar applied is the pressure of choice.

Example 13

The pearl milled suspension of Apigenin and the suspensions homogenized were investigated regarding their stability applying an electrolyte stress test using calcium chloride. One volume part of 200 mMol calcium chloride solution was admixed to one volume part of suspension, yielding a final concentration of 100 mMol calcium chloride in the suspensions. This is known to reduce drastically the zeta potential, i.e. the electrostatic repulsion leading to particle aggregation. In case a suspension is a priori more physically stable, this leads to less pronounced increase in the particle size and a more stable suspension. Particle size was measured immediately after admixing the electrolyte solution.

To detect larger sizes particles—due to the limitations of the PCS measuring range (appr. 3 nm-3 μm)—laser diffractometry (LD) was employed. The most sensitive diameter to detect aggregation is the diameter 99% (D99%), this parameter was therefore selected to judge the stability of the suspensions in the electrolyte stress test. LD diameters were calculated using the Fraunhofer theory.

The suspensions were analyzed by LD after preparation, revealing a D99% of 2.447 μm for the pearl-milled suspension. The diameters 99% for the suspensions pearl-milled and subsequently homogenized were slightly lower, but not that much different: 2.415 μm, 2.391 μm and 2.355 μm, for the suspensions produced with 100 bar, 1,000 bar and 1,500 bar respectively.

Addition of the electrolyte solution in the stability stress test lead to an increase in D99% being most pronounced for the pearl milled suspension, homogenization of the pearl milled product obviously made it more stable. The suspension pearl-milled and subsequently homogenized at 1,500 bar stayed practically unchanged.

| Suspension | | D99% before | D99% after CaCl$_2$ addition |
|---|---|---|---|
| pearl-milled only | | 2.447 μm | 4.373 μm |
| 1 Cycle | 100 bar | 2.415 μm | 3.439 μm |
| 1 Cycle | 1,000 bar | 2.391 μm | 2.612 μm |
| 1 Cycle | 1,500 bar | 2.355 μm | 2.272 μm |

Example 14

5% Rutin micro-sized powder was dispersed in water, shaken and subsequently centrifuged at 4,000 rpm and then filtered through a 0.45 μm filter to remove any potential non-dissolved fine crystals. A Rutin nanosuspension was treated the same way but using a 0.2 μm filter. HPLC analysis was performed in the clear filtrates, yielding a concentration 0.0079% in case of the microcrystalline Rutin suspension and 0.0123% in case of the Rutin nanosuspension, that means the nanocrystals possess a higher saturation solubility due to their small size in addition to the higher dissolution velocity due to the enlarged surface area.

Example 15

Various formulations were investigated regarding their photo-protective potential after topical application in vivo. These formulations contained antioxidants and the photo-protective potential was evaluated by assessing the MED for generating an UV erythem (MED—minimal dose required for generating an erythem, minimal erythem dose). The sun susceptibility of the skin of volunteers was assessed after four times of application (once daily) of the formulations in comparison to untreated skin. Based on this a sun protection factor (SPF) was calculated.

The formulations investigated were:

Nanosuspension containing 5% Rutin in form of nanocrystals, stabilizer 1.0% poloxamer 188 (NSR—nanosuspension Rutin)

Nanosuspension containing 5% of Hesperidin, stabilizer 1.0% poloxamer 188 (NSH—nanosuspension Hesperidin)

α-tocopherol acetate formulation was prepared in a concentration of 5% dissolved in liquid paraffin and used as a reference.

α-G Rutin PS (AGRPS) was dissolved in demineralized water (6% being equivalent to 5% Rutin, because the Rutin in the molecule is equivalent to 80%, 20% are saccharides) and used as a reference.

The study was performed as a placebo controlled double blind study. Three male and three female volunteers with normal skin of photo type II to III took part. The medium age of the female volunteers was 49.6±9.8 years (38.8-57.4 years). Topical application of the formulations took place on 4 subsequent days (2 mg/cm$^2$), once daily. On day 4 eradiation by UV was performed 15 minutes after application of the formulations to the skin using a sun simulator SU6p (m.u.t. GmbH, Wedel/Germany). The sun simulator created 6 single doses with a geometric increment of 25%. The 5 test areas were on the back of the volunteers (4 areas for the formulations, 1 untreated control area).

The single application of the test formulations with Rutin and Hesperidin increased the minimal erythem dose (MED) in comparison to the untreated control. A sun protection factor was defined as the ratio of the MED of the formulation treated area to the MED of the untreated area. The MED values were 1.59±0.50 for nanosuspension with Rutin 5% (NSR), 1.36±0.32 for the Hesperidin nanosuspension (NSH) and 1.27±0.31 for the water soluble α-G Rutin PS (AGRPS).

The formulation with α-tocopherol acetate led to a decrease of the MED in comparison to the untreated area, that means the skin was even more sensitive to UV radiation. The calculated SPF was 0.85±0.23.

As a summary daily application of the formulations with Rutin and Hesperidin reduced the sensitivity to UV radiation, the MED increased being most pronounced for Rutin and Hesperidin in nanocrystal formulations. All formulations with Rutin and Hesperidin possess a high photo-protective potential. The Rutin nanocrystals are much more efficient than the reference water-soluble Rutin derivative. The concentration of dissolved Rutin in the Rutin nanosuspension was in the range of the saturation solubility, that means 0.0123% (example 14). This is a factor of 1/500 lower than the dissolved concentration of the reference water soluble Rutin derivative being 5.0%. Despite having a 1/500 lower concentration of dissolved active molecules in the formulation, the Rutin nanocrystal suspensions proved to have a 25% higher SPF.

In contrast, daily application of just over a period of 4 days was obviously not sufficient to lead to a photo-protection, when using the established reference antioxidant α-tocopherol acetate. Obviously high levels in the skin sufficient to be photo-protective could not be generated and sub-doses lead even to an undesirable increase in skin sensitivity to UV radiation.

Example 16

The nanosuspension of ascorbylpalmitate from example 3 was incorporated into hydrogels. Hydrogels were prepared from poloxamer 407, xanthan gum and polyacrylate (Carbopol 981). The concentrations of the gel forming agent were 20%, 2% and 2%, respectively. The final concentration of ascorbylpalmitate after admixing the nanosuspension to the hydrogel was 2% of nanocrystals in the gel. Admixing the nanocrystals to the gel did not change significantly the LD data. The LD diameter 50% of the nanosuspension prior to admixing was 0.310 µm, after admixing the diameters 50% of the nanocrystals were 0.371 µm, 0.381 µm and 0.340 µm, respectively.

Example 17

Figure 2:
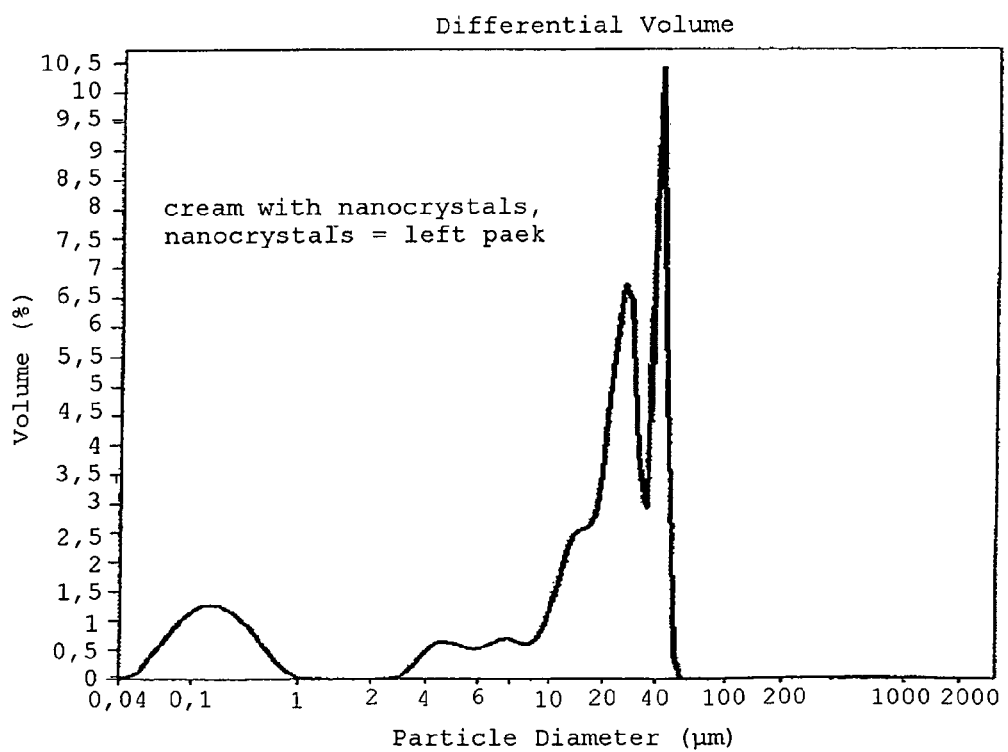
FIG. 2 illustrates the size distribution of hydrophilic water-containing cream after incorporation of nanocrystals into the cream yielding an additional peak in the lower nanometer range (size analysis: laser diffractometry, Mie theory).

Hydrophilic cream (Unguentum emulsificans) was prepared according to the German Pharmacopoeia containing emulsifying cetylstearile alcohol (Lanette N) 30 parts, liquid paraffin (paraffinum subliquidum) 35 parts and pretolatum (vaselinum) 35 parts. To 30 parts of the cream 70 parts of distilled water were added under stirring at elevated temperature to produce the hydrophilic water-containing cream (Unguentum emulsificans aquosum) of the German Pharmacopoeia. This cream was mixed in a ratio 1:1 with Rutin nanocrystal suspension (20% Rutin) under further homogenization. Size analysis by laser diffractometry of the o/w cream shows only the peak for the oil droplets, FIG. 1, the nanocrystal-containing o/w cream has a second peak in the lower nanometer range from the drug nanocrystals (FIG. 2, y-axis: probability; x-axis: size (µm)). The admixing of the Tween 80 containing nanocrystal suspension lead further to a decrease of the droplet size.

While the claimed invention has been described in detail and with reference to specific embodiments thereof, it will be apparent to one of ordinary skill in the art that various changes and modifications can be made to the claimed invention without departing from the spirit and scope thereof.

The invention claimed is:

1. A method for producing a formulation for topical application to the skin or mucosal surfaces, comprising the steps of:
   suspending a powder comprising a cosmetic or pharmaceutical active in an aqueous or non-aqueous dispersion medium being at least one of an aqueous phase or lipidic phase of a monophasic system, an aqueous phase or lipidic phase of an oil-in water emulsion, water-in-oil emulsion, microemulsion, liposomal dispersion or a macrosuspension, and containing at least one stabilizer to produce a suspension, wherein the active has a solubility in the dispersion medium of less than 10 mg/ml, wherein the stabilizer comprises at least one surfactant;
   passing the suspension through a pearl or ball mill at least one pass to produce a pre-milled suspension; and
   subjecting the pre-milled suspension to high pressure homogenization at a pressure of 100-500 bar for at least one cycle to produce a dispersion of particles of the cosmetic or pharmaceutical active in the nanometer range, having a Photon Correlation Spectroscopy (PCS) size below 1000 nm, wherein the concentration of the dispersed active in the aqueous phase or in the lipidic phase is above the saturation concentration of active material, which formulation provides penetration of the cosmetic or pharmaceutical active into the skin.

2. A method according to claim 1, wherein the stabilizer comprises at least one surfactant selected from the group consisting of lauryl glucoside, Decyl Glucoside, Sodium cocoamphoacetate, polyglyceryl 3-methylglucose distearate, cetearyl glucoside, Inulin Lauryl Carbamate, lecithin and its derivatives, purified phospholipids, polyethylene glycol sorbitanoleate and mixtures thereof.

3. A method according to claim 1, wherein the stabilizer comprises at least one viscosity enhancer.

4. A method according to claim 1, wherein the stabilizer comprises at least one viscosity enhancer selected from the group consisting of silicium dioxide, xanthan gum, ethylcellulose, polyacrylates, aluminium monostearate, solid lipids, carnauba wax, bees wax, and hard fats.

5. A method according to claim 1, wherein the stabilizer comprises at least one anti-flocculant.

6. A method according to claim 1, wherein the stabilizer comprises at least one anti-flocculant selected from the group consisting of sodium citrate, sodium hydrogen phosphate, sodium hydrogen diphosphate, and sodium pyrophosphate.

7. A method according to claim 1, wherein the stabilizer comprises at least one steric stabilizer.

8. A method according to claim 1, wherein the stabilizer comprises at least one steric stabilizer selected from the group consisting of natural or synthetic polymers, polyvinyl alcohol, polyvinyl pyrrolidone (PVP), Poloxamer polymers, and copolymers of polyoxyethylene and polyoxypropylene.

9. A method according to claim 1, wherein the stabilizer comprises at least one crystal growth inhibitor.

10. A method according to claim 1, wherein the stabilizer comprises at least one crystal growth inhibitor selected from the group consisting of polyvinyl pyrrolidone (PVP), cellulose derivatives, HPMC (hydroxypropylmethylcellulose), and HPMCAS (hydroxypropyl-methylcelluloseacetatesuccinate).

11. A method according to claim 1, wherein the stabilizer comprises at least one nucleation inhibitor.

12. A method according to claim 11, wherein the nucleation inhibitor comprises at least one bile salt.

13. A method according to claim 1, wherein the high pressure homogenizer comprises at least one of piston gap homogenizers and jet stream homogenizers.

14. A method according to claim 1, wherein the pearl milling and/or the high pressure homogenization are performed at or below 10° C.

15. The method according to claim 1, wherein the step of subjecting the pre-milled suspension to high pressure homogenization is conducted at a temperature below 20° C.

16. A method according to claim 15, wherein the high pressure homogenization temperature is below 10° C.

17. A method according to claim 15, wherein the solubility of the active in the dispersion medium is below 0.1 mg/ml.

18. A method according to claim 15, wherein the solubility of the active in the dispersion medium is below 0.01 mg/ml (10 μg/ml).

19. A method according to claim 15, wherein the particles have a PCS size below 500 nm.

20. A method according to claim 15, wherein the particles have a PCS size below 200 nm.

21. A method according to claim 15, wherein the particles have a PCS size below 100 nm.

22. A method according to claim 15, wherein the particle concentration is at least 3 times greater than the saturation solubility of the active in the dispersion medium.

23. A method according to claim 15, wherein the particle concentration is at least 5 times greater than the saturation solubility of the active in the dispersion medium.

24. A method according to claim 15, wherein the particle concentration is 10 to 50 times greater than the saturation solubility of the active in the dispersion medium.

25. A method according to claim 15, wherein the active comprises at least one selected from the group consisting of Catechines, flavonoids, isoflavones, and cumarines.

26. A method for producing a formulation for topical application to the skin or mucosal surfaces, comprising the steps of:
suspending a powder comprising a cosmetic or pharmaceutical active in an aqueous or non-aqueous dispersion medium being at least one of an aqueous phase or lipidic phase of a monophasic system, an aqueous phase or lipidic phase of an oil-in water emulsion, water-in-oil emulsion, microemulsion, liposomal dispersion or a macrosuspension, and containing at least one stabilizer to produce a suspension, wherein the active has a solubility in the dispersion medium of less than 10 mg/mL;
passing the suspension through a pearl or ball mill at least one pass to produce a pre-milled suspension; and
subjecting the pre-milled suspension to high pressure homogenization at a pressure of 100-500 bar for at least one cycle to produce a dispersion of particles of the cosmetic or pharmaceutical active in the nanometer range, having a Photon Correlation Spectroscopy (PCS) size below 1000 nm, wherein the concentration of the dispersed active in the aqueous phase or in the lipidic phase is above the saturation concentration of active material, which formulation provides penetration of the cosmetic or pharmaceutical active into the skin, wherein the pearl milling and/or the high pressure homogenization are performed at or below room temperature of 20° C.

* * * * *